(12) United States Patent
Peter et al.

(10) Patent No.: US 10,711,269 B2
(45) Date of Patent: Jul. 14, 2020

(54) METHOD FOR MAKING AN ASYMMETRICALLY-TAGGED SEQUENCING LIBRARY

(71) Applicant: Agilent Technologies, Inc., Santa Clara, CA (US)

(72) Inventors: Brian Jon Peter, Los Altos, CA (US); David Taussig, Sunnyvale, CA (US); Bahram Arezi, Carlsbad, CA (US); Robert A. Ach, San Francisco, CA (US); Nicholas M. Sampas, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 615 days.

(21) Appl. No.: 15/409,124

(22) Filed: Jan. 18, 2017

(65) Prior Publication Data

US 2018/0201924 A1 Jul. 19, 2018

(51) Int. Cl.
*C12N 15/10* (2006.01)
*C12Q 1/6806* (2018.01)

(52) U.S. Cl.
CPC ....... *C12N 15/1065* (2013.01); *C12Q 1/6806* (2013.01)

(58) Field of Classification Search
None
See application file for complete search history.

(56) References Cited

U.S. PATENT DOCUMENTS

| 6,287,825 | B1 | 9/2001 | Weissman et al. |
| 2012/0244525 | A1 | 9/2012 | Hendrickson |
| 2013/0029380 | A1 | 1/2013 | Mikawa |
| 2015/0197786 | A1 | 7/2015 | Osborne et al. |
| 2015/0275285 | A1 | 10/2015 | Zhang |
| 2016/0053253 | A1 * | 2/2016 | Salathia et al. .... C12N 15/1096 506/4 |
| 2016/0355880 | A1 | 12/2016 | Gormley et al. |

FOREIGN PATENT DOCUMENTS

| WO | 2008015396 A2 | 2/2008 | |
| WO | WO-2008015396 A2 * | 2/2008 | .......... C12Q 1/6855 |
| WO | 2015148219 A1 | 1/2015 | |
| WO | WO-2015148219 A1 * | 10/2015 | |

OTHER PUBLICATIONS

Monson-Miller, et al., "Reference genome-independent assessment of mutation density using restriction enzyme-phased sequencing", BMC Genomics, 2012, 13:72.

* cited by examiner

*Primary Examiner* — Kaijiang Zhang
(74) *Attorney, Agent, or Firm* — Stinson LLP

(57) ABSTRACT

A method for making an asymmetrically-tagged sequencing library is provided. In some embodiments, the method may comprise: obtaining a symmetrically-tagged library of cDNA or genomic DNA fragments, hybridizing a tailed first primer to the 3' sequence tag of the library and extending the same to produce primer extension products, and amplifying the primer extension products using a pair of tailed primers to produce asymmetrically-tagged library.

20 Claims, 9 Drawing Sheets

Specification includes a Sequence Listing.

SEQUENCE LISTING

<160> NUMBER OF SEQ ID NOS: 20

<210> SEQ ID NO 1
<211> LENGTH: 47
<212> TYPE: DNA
<213> ORGANISM: artificial sequence
<220> FEATURE:
<223> OTHER INFORMATION: synthetic oligonucleotide

<400> SEQUENCE: 1
tagcttggct atcgacacca taaggcgaac ttgtgatcaa gagacag                47

<210> SEQ ID NO 2
<211> LENGTH: 48
<212> TYPE: DNA
<213> ORGANISM: artificial sequence
<220> FEATURE:
<223> OTHER INFORMATION: synthetic oligonucleotide

<400> SEQUENCE: 2
ctaatctgat ggacggacac acgtactaga cttgtgatca agagacag                48

<210> SEQ ID NO 3
<211> LENGTH: 48
<212> TYPE: DNA
<213> ORGANISM: artificial sequence
<220> FEATURE:
<223> OTHER INFORMATION: synthetic oligonucleotide

<400> SEQUENCE: 3
cgatagttat gcgagcacca ctaggcatga cttgtgatca agagacag                48

<210> SEQ ID NO 4
<211> LENGTH: 47
<212> TYPE: DNA
<213> ORGANISM: artificial sequence
<220> FEATURE:
<223> OTHER INFORMATION: synthetic oligonucleotide

<400> SEQUENCE: 4
gatgtgatcg taccgacaca ggactcctac ttgtgatcaa gagacag                 47

<210> SEQ ID NO 5
<211> LENGTH: 47
<212> TYPE: DNA
<213> ORGANISM: artificial sequence
<220> FEATURE:
<223> OTHER INFORMATION: synthetic oligonucleotide

<400> SEQUENCE: 5
agttcatgac gtgtgaccac ctctctatac ttgtgatcaa gagacag                 47

<210> SEQ ID NO 6
<211> LENGTH: 47
<212> TYPE: DNA
<213> ORGANISM: artificial sequence
<220> FEATURE:
<223> OTHER INFORMATION: synthetic oligonucleotide

<400> SEQUENCE: 6
caggagtccg ttatcacaca tatcctctac ttgtgatcaa gagacag                 47

<210> SEQ ID NO 7
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 7
attcagtgag atgcaccaca cagagtaagg cgaacttgtg atcaagagac ag           52

<210> SEQ ID NO 8

```
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 8
attcagtgag atgcaccaca cagagcgtac tagacttgtg atcaagagac ag         52

<210> SEQ ID NO 9
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 9
attcagtgag atgcaccaca cagagtaggc atgacttgtg atcaagagac ag         52

<210> SEQ ID NO 10
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 10
attcagtgag atgcaccaca cagagggact cctacttgtg atcaagagac ag         52

<210> SEQ ID NO 11
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 11
attcagtgag atgcaccaca cagagctctc tatacttgtg atcaagagac ag         52

<210> SEQ ID NO 12
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 12
attcagtgag atgcaccaca cagagtatcc tctacttgtg atcaagagac ag         52

<210> SEQ ID NO 13
<211> LENGTH: 61
<212> TYPE: DNA
<213> ORGANISM: artificial sequence
<220> FEATURE:
<223> OTHER INFORMATION: synthetic oligonucleotide

<400> SEQUENCE: 13
caagcagaag acggcatacg agatagtccg acgatcattc agtgagatgc accacacaga   60
g                                                                  61

<210> SEQ ID NO 14
<211> LENGTH: 65
<212> TYPE: DNA
<213> ORGANISM: artificial sequence
<220> FEATURE:
<223> OTHER INFORMATION: synthetic oligonucleotide
```

<400> SEQUENCE: 14
aatgatacgg cgaccaccga gatctacacc gacaggttca gtagcttggc tatcgacacc    60
ataag    65

<210> SEQ ID NO 15
<211> LENGTH: 66
<212> TYPE: DNA
<213> ORGANISM: artificial sequence
<220> FEATURE:
<223> OTHER INFORMATION: synthetic oligonucleotide

<400> SEQUENCE: 15
aatgatacgg cgaccaccga gatctacacc gacaggttca gctaatctga tggacggaca    60
cacgta    66

<210> SEQ ID NO 16
<211> LENGTH: 66
<212> TYPE: DNA
<213> ORGANISM: artificial sequence
<220> FEATURE:
<223> OTHER INFORMATION: synthetic oligonucleotide

<400> SEQUENCE: 16
aatgatacgg cgaccaccga gatctacacc gacaggttca gcgatagtta tgcgagcacc    60
actagg    66

<210> SEQ ID NO 17
<211> LENGTH: 65
<212> TYPE: DNA
<213> ORGANISM: artificial sequence
<220> FEATURE:
<223> OTHER INFORMATION: synthetic oligonucleotide

<400> SEQUENCE: 17
aatgatacgg cgaccaccga gatctacacc gacaggttca ggatgtgatc gtaccgacac    60
aggac    65

<210> SEQ ID NO 18
<211> LENGTH: 65
<212> TYPE: DNA
<213> ORGANISM: artificial sequence
<220> FEATURE:
<223> OTHER INFORMATION: synthetic oligonucleotide

<400> SEQUENCE: 18
aatgatacgg cgaccaccga gatctacacc gacaggttca gagttcatga cgtgtgacca    60
cctct    65

<210> SEQ ID NO 19
<211> LENGTH: 65
<212> TYPE: DNA
<213> ORGANISM: artificial sequence
<220> FEATURE:
<223> OTHER INFORMATION: synthetic oligonucleotide

<400> SEQUENCE: 19
aatgatacgg cgaccaccga gatctacacc gacaggttca gcaggagtcc gttatcacac    60
atatc    65

<210> SEQ ID NO 20

```
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 20
ctgtctcttg atcacaagt                                              19
```

METHOD FOR MAKING AN ASYMMETRICALLY-TAGGED SEQUENCING LIBRARY

BACKGROUND

Many Next-Generation Sequencing (NGS) platforms require asymmetrically-tagged fragments, i.e., DNA fragments that are flanked by different adaptor sequences. The adapter sequences are necessary for clonal amplification on the flow cell surface, and may also be used as priming sites for insert or barcode or sample index sequences. For example, in Illumina's system, the fragments have the P5 sequence on one end and the P7 sequence on the other. Such molecules are not straightforward to produce efficiently, largely because most of the methods that are used to add adaptor sequences to fragments do so in a random way. If the adaptor sequences are added in a random way, only 50% of the tagged fragments are asymmetrically tagged with the correct sequences (e.g., the fragments have P5 at one end and P7 at the other); the other 50% of the tagged sequences are symmetrically tagged (e.g., the fragments have P5 at both ends or P7 at both ends). Only the asymmetrically fragments are suitable for sequencing on many sequencing platforms.

When sequencing the genome of a single cell or a small number of cells, the 50% loss of coverage caused by the randomness of adaptor attachment is a serious problem. For this reason, new strategies need to be developed.

SUMMARY

This disclosure provides, among other things, a method for making an asymmetrically-tagged sequencing library from a symmetrically-tagged sequencing library. In some embodiments, the method may comprise: obtaining a symmetrically-tagged library of cDNA or genomic DNA fragments, hybridizing a tailed first primer to the 3' sequence tag of the library and extending the same to produce primer extension products, and amplifying the primer extension products using a pair of tailed primers to produce asymmetrically-tagged library.

In some embodiments, the method may comprise: (a) obtaining a symmetrically-tagged library of cDNA or genomic DNA fragments, wherein at least some of the members of the library comprise a top strand comprising a 5' sequence tag and a 3' sequence tag, wherein the 5' and 3' sequence tags complementary sequences; (b) hybridizing a first primer to the 3' sequence tag of the library, wherein the first primer comprises a 3' region which is complementary to the 3' sequence tag of the library, and a 5' non-complementary tail; (c) extending the first primer to produce primer extension products that comprises, from 5' to 3', the sequence of the first primer, a sequence of a fragment, and the complement of a 5' sequence tag of (a); and (d) amplifying the primer extension products of (c) using: i. a forward primer of formula A4-A3, wherein sequence A4 is a 5' tail and sequence A3 is contained in the sequence of the first primer; and ii. a reverse primer of formula A5-A2, wherein sequence A5 is a 5' tail and sequence A2 is contained in the 5' sequence tag of (a); to produce an asymmetrically-tagged library in which at least some of the members comprise a top strand comprising i. a first end comprising sequence A5, ii. the sequence of a fragment, and iii. a second end comprising the complement of sequence A4.

Other compositions, systems, methods, features and advantages of the invention will be or will become apparent to one with skill in the art upon examination of the following figures and detailed description. It is intended that all such additional systems, methods, features and advantages be included within this description and be within the scope of the invention.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
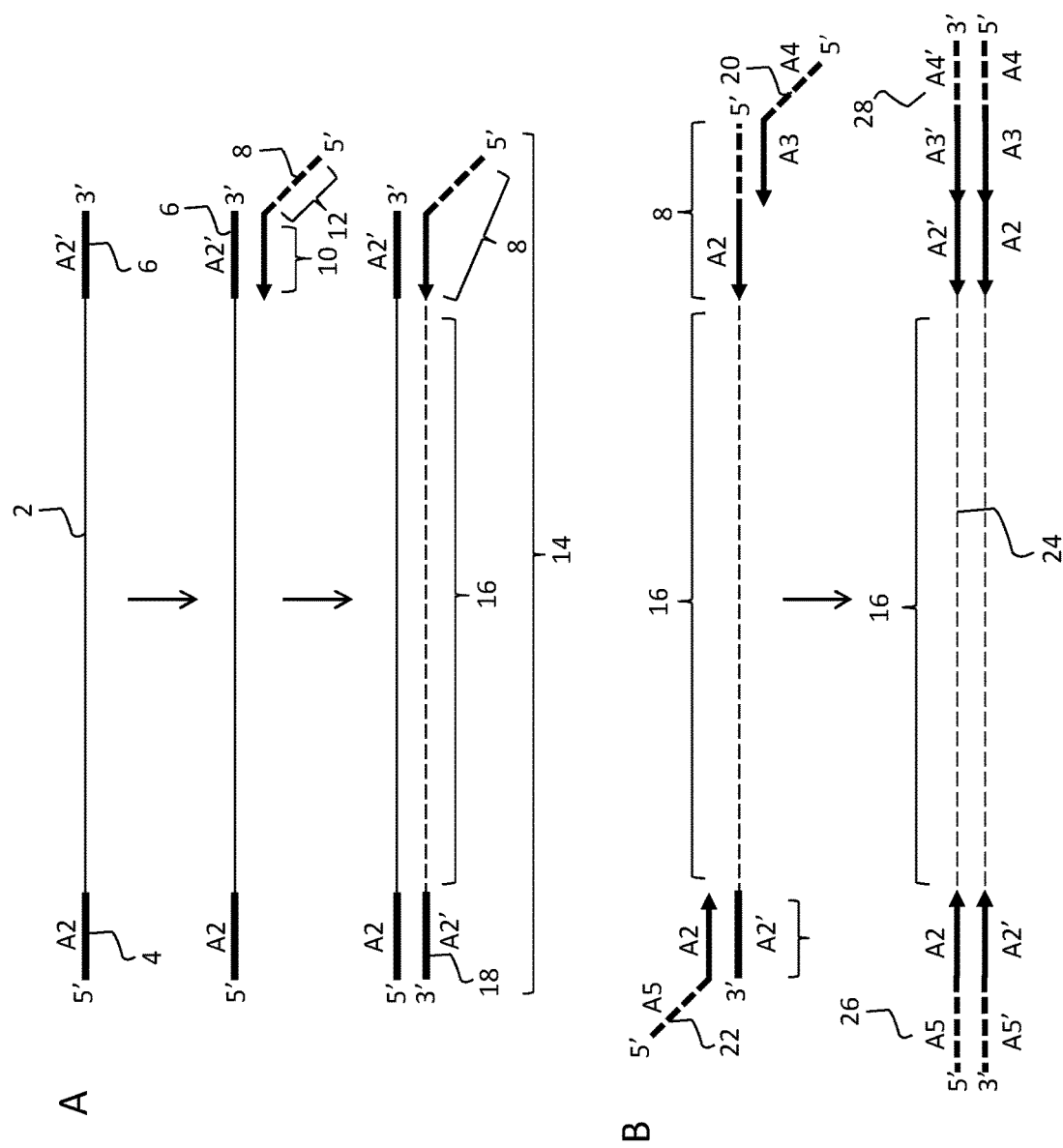
FIG. 1 panels A and B schematically illustrate some of the principles of an embodiment of the present method.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "Oligonucleotide Synthesis: A Practical Approach" 1984, IRL Press, London, Nelson and Cox (2000), Lehninger, A., *Principles of Biochemistry* 3$^{rd}$ Ed., W. H. Freeman Pub., New York, N.Y. and Berg et al. (2002) *Biochemistry*, 5$^{th}$ Ed., W. H. Freeman Pub., New York, N.Y., all of which are herein incorporated in their entirety by reference for all purposes.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "sample" as used herein relates to a material or mixture of materials, typically, although not necessarily, in liquid form, containing one or more analytes of interest. In one embodiment, the term as used in its broadest sense, refers to any plant, animal or viral material containing DNA or RNA, such as, for example, tissue or fluid isolated from an individual (including without limitation plasma, serum, cerebrospinal fluid, lymph, tears, saliva and tissue sections), from preserved tissue (such as FFPE sections) or from in vitro cell culture constituents, as well as samples from the environment.

The term "nucleic acid sample," as used herein denotes a sample containing nucleic acids. A nucleic acid samples used herein may be complex in that they contain multiple different molecules that contain sequences. Genomic DNA samples from a mammal (e.g., mouse or human) are types of complex samples. Complex samples may have more than $10^4$, $10^5$, $10^6$ or $10^7$ different nucleic acid molecules. Also, a complex sample may comprise only a few molecules, where the molecules collectively have more than $10^4$, $10^5$, $10^6$ or $10^7$ or more nucleotides. A DNA target may originate from any source such as genomic DNA, or an artificial DNA construct. Any sample containing nucleic acid, e.g., genomic DNA made from tissue culture cells or a sample of tissue, may be employed herein.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 11 to 30, 31 to 40, 41 to 50, 51-60, 61 to 70, 71 to 80, 80 to 100, 100 to 150 or 150 to 200 nucleotides in length, for example.

The term "primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42 C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to the process of synthesizing nucleic acid molecules that are complementary to one or both strands of a template nucleic acid. Amplifying a nucleic acid molecule may include denaturing the template nucleic acid, annealing primers to the template nucleic acid at a temperature that is below the melting temperatures of the primers, and enzymatically elongating from the primers to generate an amplification product. The denaturing, annealing and elongating steps each can be performed one or more times. In certain cases, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly, if a unique identifier, e.g., a barcode is used, the unique identifier is usually read to identify, for example, an object or file associated with the unique identifier.

In certain cases, an oligonucleotide used in the method described herein may be designed using a reference genomic region, i.e., a genomic region of known nucleotide sequence, e.g., a chromosomal region whose sequence is deposited at NCBI's GenBank database or other database, for example. Such an oligonucleotide may be employed in an assay that uses a sample containing a test genome, where the test genome contains to binding sites for sequences in the oligonucleotide.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

An "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "genotyping", as used herein, refers to any type of analysis of a nucleic acid sequence, and includes sequencing, polymorphism (SNP) analysis, and analysis to identify rearrangements.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, Pacific Bio, and Roche etc. Next-generation sequencing methods may also include nanopore sequencing methods or electronic-detection based methods such as Ion Torrent technology commercialized by Life Technologies.

The term "extending", as used herein, refers to the extension of a primer by the addition of nucleotides using a polymerase. If a primer that is annealed to a nucleic acid is extended, the nucleic acid acts as a template for extension reaction.

The term "barcode sequence" or "molecular barcode", as used herein, refers to a sequence of nucleotides used to a) identify and/or track the source of a polynucleotide in a reaction (i.e., different samples may share common features of a barcode or index sequence, such as length, sequence, or GC content, that may serve a "sample identifier sequence") and/or b) distinguish between fragments to which the barcode has been added (e.g., may be a "molecule identifier sequence"). In use, molecular barcodes are often "degenerate" or random sequences composed of a mixture of 2, 3, or 4 bases at each position, thus creating a very diverse pool of barcode sequences. As the molecular barcode sequences are added to sequencing template, the high diversity of the pool ensures that each template molecule receives a different barcode, and hence, the barcodes can be sued to distinguish individual template molecules. Molecule identifier sequences allow one to group the sequence reads that are obtained from copies of an initial molecule, which may be useful for accurate counting of template molecules, or detection of errors which arise during amplification. A barcode sequence can have a length in range of from 4 to 36 nucleotides, or from 6 to 30 nucleotides, or from 8 to 20 nucleotides.

The term "sample identifier sequence," "sample index," or "sample barcode" is a type of barcode that can be appended to a target polynucleotide, where the sequence identifies the source of the target polynucleotide (i.e., the sample from which sample the target polynucleotide is derived). Sample barcodes or indexes are typically known sequences (e.g., 96 different, orthogonal, 8-nucleotide sequences maye be used to distinguish 96 samples pooled into one reaction. In use, each sample can be tagged with a different sample identifier sequence (e.g., one sequence is appended to each sample, where the different samples are appended to different sequences), and the tagged samples are pooled. After the pooled sample is sequenced, the sample identifier sequence can be used to identify the source of the sequences.

The term "molecule identifier sequence" refers to a type of molecular barcode that has complexity that is sufficient to help one distinguish between fragments to which the barcode has been added. Fragments are that are tagged with a molecular identifier sequence can be amplified and sequenced. The molecule identifier sequence allows one to determine which sequence reads are from the same initial fragment. In some embodiments, a high complexity molecular barcode may be used (e.g., one that is composed of at least 10,000 or 100,000 sequences). In other embodiments, some fragments may be tagged with the same molecular barcode, but those fragments can still be distinguished by, e.g., any combination of i. the molecular barcode sequence, ii. the sequence of the fragment, iii. the sequence of the ends of the fragment, and/or iv. the site of insertion of the molecular barcode into the fragment. In some embodiments, at least 95%, e.g., at least 96%, at least 97%, at least 98%, at least 99% or at least at least 99.5% of the target polynucleotides become associated with a different molecular barcode sequence. In some embodiments a molecular barcode may comprise one or more (e.g., at least 2, at least 3, at least 4, at least 5, or 5 to 30 or more) nucleotides selected from R, Y, S, W, K, M, B, D, H, V, N (as defined by the IUPAC code). In some embodiments, a molecular barcode may comprise a degenerate or random sequence (e.g., an oligonucleotide that has a run of 4-10 "Ns") Barcode sequences may vary widely in size and composition; the following references provide guidance for selecting sets of barcode sequences appropriate for particular embodiments: Casbon (Nuc. Acids Res. 2011, 22 e81), Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's GenBank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The terms "reverse primer" and "forward primer" refer to primers that hybridize to different strands in a double-stranded DNA molecule, where extension of the primers by a polymerase is in a direction that is towards the other primer.

The term "symmetrically-tagged" refers to fragments that have the same adaptor at both ends. In a symmetrically-tagged library, the adaptor sequence at the 5' end of the top strand is complementary to the adaptor sequence at the 3' end of the top strand. Symmetrically-tagged fragments may be amplified by PCR using a single forward primer that hybridizes to the adaptors, but the amplification is typically less efficient because the template molecule can fold back on itself, allowing the end sequences to hybridize, and competing with primers for binding. In some cases, this "PCR suppression" effect can be overcome by changing PCR conditions to enable better primer binding, increasing the concentration of primers, or changing the relative lengths or sequence content of the primers or primer binding sequences. The term "same barcode on both strands" and grammatical equivalents thereof refers to a double stranded molecule that has a barcode sequence covalently linked at the 5' end of one strand and the complement of the barcode sequence covalently linked at the 3' end of the other strand.

The term "adaptor" refers to a nucleic acid that can be covalently joined, via a ligase, transposase, or other chemical or enzymatic reaction, to at least one strand of a double-stranded DNA molecule. The term "adaptor" refers to molecules that are at least partially double-stranded. An adaptor may be 40 to 150 bases in length, e.g., 50 to 120 bases, although adaptors outside of this range are envisioned.

The term "adaptor-tagged," as used herein, refers to a nucleic acid that has been tagged by an adaptor. An adaptor can be joined to a 5' end and/or a 3' end of a nucleic acid molecule.

The term "tagged DNA" as used herein refers to DNA molecules that have an added adaptor sequence, i.e., a "tag" of synthetic origin. An adaptor sequence can be added (i.e., "appended") by a ligase or transposase.

The terms "5' sequence tag" and "3' sequence tag" refer to sequences that have been added (i.e., appended by a ligase or transposase) to the ends of a fragment. Tag sequences are typically in the range of 12-100 nucleotides in length and, as would be apparent, do not cross-hybridize that with other sequences in the genome or cDNA sample being studied. For example, a sequence tag does not contain a sequence of at least 10, at least 12 or at least 15 contiguous nucleotides this complementary to a sequence in the genome or cDNA sample being studied.

The term "asymmetrically-tagged" refers to fragments that have a different adaptor sequence at each end. In an asymmetrically-tagged library, the adaptor sequence at the 5' end of the top strand is not complementary to the adaptor sequence at the 3' end of the top strand. An asymmetrically tagged fragment can be amplified by two primers: one that hybridizes to a first tag sequence added to the 3' end of a strand, and another that hybridizes to the complement of a second tag sequence added to the 5' end of a strand. Asymmetrically-tagged fragments can be made by ligating them to a "Y-adaptor" or a hairpin loop adaptor (which can be cleaved, after ligation, to produce a "Y-adaptor"), where such terms refer to an adaptor that contains: a double-stranded region and a single-stranded region in which the opposing sequences are not complementary. The end of the double-stranded region may be or can be joined to target molecules such as double-stranded fragments of genomic DNA, e.g., by via a ligase or transposase-catalyzed reaction. Each strand of an adaptor-tagged double-stranded DNA that has been joined to a Y adaptor is asymmetrically tagged in that it has the sequence of one strand of the Y-adaptor at one end and the other strand of the Y-adaptor at the other end. Asymmetrically tagged fragments can be made by tagmentation, using a transposon that has been loaded with a mix of two transposon ends, the first transposon ends adding a one tag sequence and the second transposase adding the other tag sequence. Asymmetrically tagged fragments can also be made by ligation of target fragments to two or more adapter sequences.

The terms "tail" refers to a sequence in the 5' region of a primer that does not hybridize to the same sequence as the 3' region of the primer (i.e., at least 10, at least 12 or at least 15 nucleotides at the 3' end of the primer). Primers that contain a 5' tail contain at least two regions: a first region at the 3' end of the primer that hybridizes to a target sequence and a second region, which is 5' to the 3' region, which does not hybridize to the target sequence. As will be described in greater detail below, a 5' tail can provide a primer binding site, thereby allowing an extension product containing the primer to be amplified by another primer. Tails are "non-complementary" in the sense that they are designed to be not complementary to any other sequences in the genome or cDNA under study.

The terms "variable" and "varies", in the context of two or more nucleic acid sequences that are variable, refers to two or more nucleic acids that have different sequences relative to each another. In other words, if the polynucleotides of a population have a variable sequence, then the nucleotide sequence of the polynucleotide molecules of the population varies from molecule to molecule. The term "variable" is not to be read to require that every molecule in a population has a different sequence to the other molecules in a population.

The term "complexity" refers the total number of different sequences in a population. For example, if a population has 4 different sequences then that population has a complexity of 4. A population may have a complexity of at least 4, at least 8, at least 16, at least 100, at least 1,000, at least 10,000 or at least 100,000 or more, depending on the desired result.

The term "the sequence of a barcode", as used herein, refers to the sequence of nucleotides that makes up the barcode. The sequence of a barcode may be at least 3 nucleotides in length, more usually 5-30 or more nucleotides in length.

The terms "tagmentation" and "tagmenting" refer to the simultaneous transposase-catalyzed fragmentation and tagging of a double-stranded DNA sample, as described by, e.g., Picelli et al, Genome Res. 2014 24: 2033-40; Adey et al, Genome Biol. 2010 11:R119 and Caruccio et al, Methods Mol. Biol. 2011 733: 241-55, US20100120098 and US20130203605). Kits for performing tagmentation are commercially sold under the tradename NEXTERA™ by Illumina (San Diego, Calif.).

Certain polynucleotides described herein may be referred by a formula (e.g., "A4-A3"). Unless otherwise indicated the polynucleotides defined by a formula is oriented in the 5' to 3' direction. The components of the formula, e.g., "A4", "A3", etc., refer to separately definable sequences of nucleotides within a polynucleotide, where, unless implicit from the context, the sequences are linked together covalently such that a polynucleotide described by a formula is a single molecule. In many cases the components of the formula are immediately adjacent to one another in the single molecule. Following convention, the complement of a sequence shown in a formula will be indicated with a prime (') such that the complement of sequence "A2" will be "A2'". Moreover, unless otherwise indicated or implicit from the context, a polynucleotide defined by a formula may have additional sequence, a primer binding site, a molecular barcode, a promoter, or a spacer, etc., at its 3' end, its 5' end or both the 3' and 5' ends. As would be apparent, the various component sequences of a polynucleotide (e.g., A2, A3, A4, etc.,) may independently be of any desired length as long as they capable of performing the desired function (e.g., hybridizing to another sequence). For example, the various component sequences of a polynucleotide may independently have a length in the range of 8-80 nucleotides, e.g., 10-50 nucleotides or 12-30 nucleotides.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Provided herein is a way for asymmetrically tagging a symmetrically-tagged genomic DNA or cDNA library. The method can be employed to analyze DNA (genomic DNA or cDNA) from virtually any organism, including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the DNA used in the method may be derived from a mammal, wherein in certain embodiments the mammal is a human. In exemplary embodiments, the sample may contain genomic DNA or cDNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, synovial fluid, urine, amniotic fluid, and semen. In particular embodiments, a sample may be obtained from a subject, e.g., a human.

In some embodiments, the sample comprises DNA fragments obtained from a clinical sample, e.g., a patient that has or is suspected of having a disease or condition such as a cancer, inflammatory disease or pregnancy. In some embodiments, the sample may be made by extracting fragmented DNA from an archived patient sample, e.g., a formalin-fixed paraffin embedded tissue sample. In other embodiments, the patient sample may be a sample of cell-free circulating DNA from a bodily fluid, e.g., peripheral blood. The DNA fragments used in the initial steps of the method can be non-amplified DNA that has not been denatured beforehand. In some cases the sample may be fragmented mechanically (e.g., by sonication, nebulization, or shearing) or enzymatically, using a double stranded DNA fragmentase enzyme (New England BioLabs, Ipswich Mass.). In other embodiments, the DNA in the initial sample may already be fragmented (e.g., as is the case for FFPE samples and circulating cell-free DNA (cfDNA), e.g., ctDNA). The method finds particular use in analyzing samples that have a limiting amount of DNA, e.g., samples that contain DNA from a single cell or a few cells (e.g., 2 to 100 cells, 2 to 50 cells or 2 to 10 cells).

As noted above, provided herein is a method for making an asymmetrically tagged library of cDNA or genomic DNA fragments from a symmetrically tagged library of cDNA or genomic DNA fragments. With reference to FIG. 1, panel A, in some embodiments the method may comprise: (a) obtaining a symmetrically-tagged library of cDNA or genomic DNA fragments, wherein at least some of the members of the library comprise a top strand or insert sequence 2 comprising a 5' sequence tag 4 and a 3' sequence tag 6, wherein the 5' and 3' sequence tags have complementary sequences. In some embodiments, the DNA fragments in this library may have a median size that is below 1 kb (e.g., in the range of 50 bp to 500 bp, 80 bp to 400 bp, or 100 to 1,000 bp), although fragments having a median size outside of this range may be used. The complementary sequences in the 5' and 3' sequence tags are referred to as A2 and A2' in FIG. 1. These sequences may be of any length, but in many embodiments they may be independently 12 to 100 nucleotides in length.

Next, the method comprises (b) hybridizing a first primer 8 to the 3' sequence tag 6 of the library, wherein the first primer 8 comprises a 3' region 10 (of at least 10, at least 12 or at least 15 nucleotides in length) which is complementary to the 3' sequence tag 6 of the library, and a 5' non-complementary tail 12, i.e., a tail that that is not complementary to either of the 3' or 5' tag sequences (or other sequence in the library). The tail may be of any suitable length, e.g., at least 10, at least 12 or at least 15 nucleotides in length).

Next, step (c) comprises extending the first primer 8 to produce primer extension products 14 that comprises, from 5' to 3', the sequence of the first primer 8, a sequence of a fragment 16, and the complement of a 5' sequence tag of step (a) 18. The amplification of primer extension products 14 is shown in panel B of FIG. 1. With reference to FIG. 1, panel B, step (d) of the method comprises amplifying the primer extension products of (c) using: i. a forward primer of formula A4-A3 20, wherein sequence A4 is a 5' tail and sequence A3 is contained in the sequence of the first primer 8; and ii. a reverse primer of formula A5-A2 22, wherein sequence A5 is a 5' tail and sequence A2 is contained in the 5' sequence tag of (a) 4. This amplification step comprises an asymmetrically-tagged library in which at least some of the members comprise a top strand 24 comprising i. a first end 26 comprising sequence A5, ii. the sequence of a fragment, and ii. a second end 28 comprising the complement of sequence A4. The dashed line for the insert sequence 16 denotes that this is a copy of the original strand 2 which may be used to differentiate these strands. For example, in some embodiments, primer extension product 14 may be synthesized with deoxyuridine in place of deoxythymidine, or other modified nucleotides, enabling later digestion, detection, or separation of the synthesized strands for decontamination or other purposes.

One feature of the invention is that it creates an asymmetrically tagged library from target fragments, but the adaptor sequence directly adjacent to the insert sequence (for example, A2 and A2' in FIG. 1, or A1 in FIG. 2) remains symmetrical. In most cases, the insert sequence 2 itself will not be symmetrical, meaning that it will have different sequence information at the 5' and 3' ends. In some embodiments, the sequence information at both ends of the target fragment 2 may be determined by annealing a sequencing primer (which may be homologous to the sequence denoted region 10 in FIG. 1) to the symmetrical adapter sequence. In these embodiments, separate clusters may be formed from each of the top and bottom strands of the duplex, and the sequence at the 5' ends of each of the top and bottom strands may be measured by annealing a primer to the symmetrical adapter sequence (for example, by annealing a primer to sequence A1' in FIGS. 2-5). In this way, paired-end sequence information may be obtained from both ends of a target fragment with a single sequencing primer.

Figure 2:
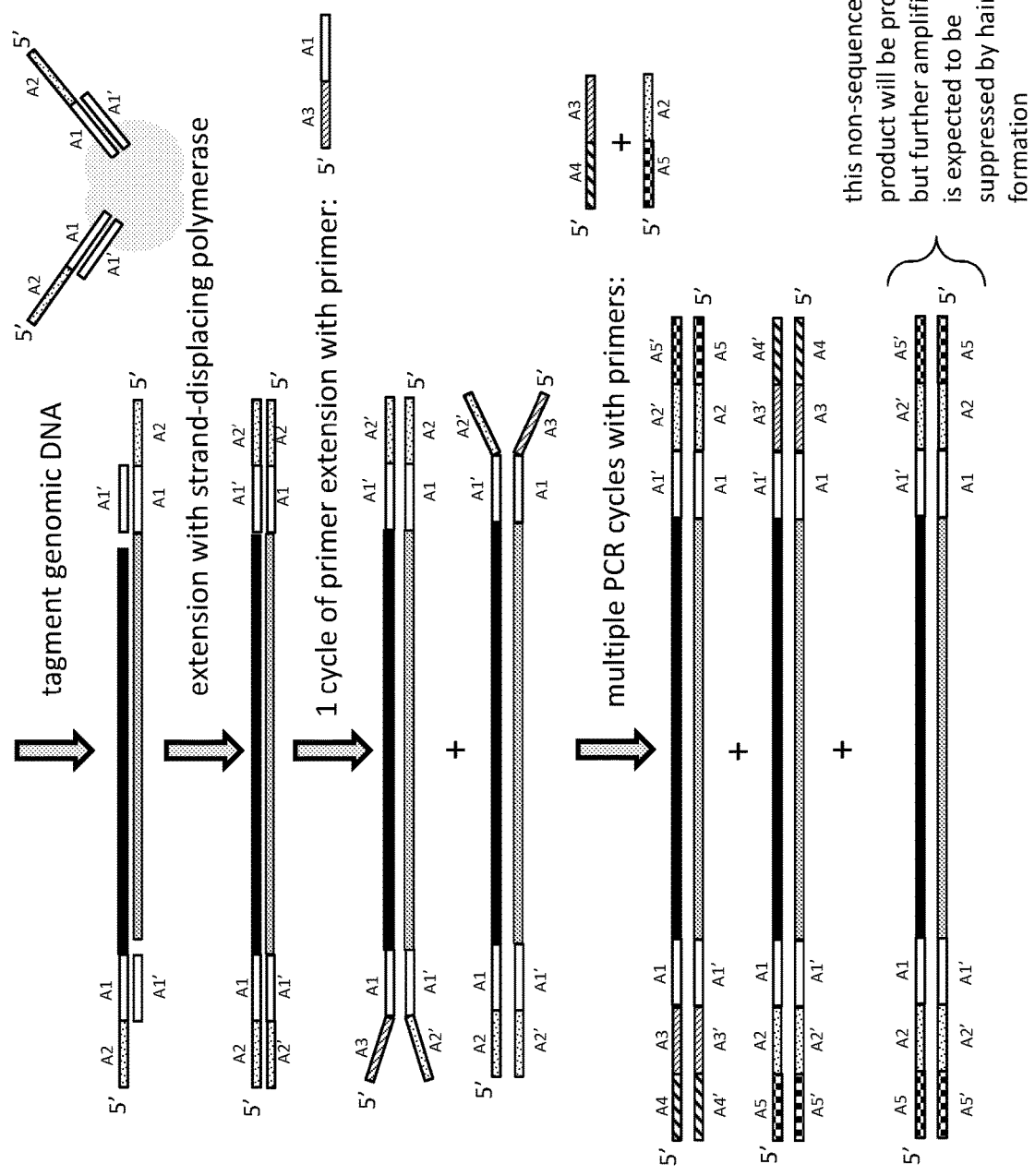
FIG. 2 schematically illustrates an exemplary transposase-based library preparation method.
Figure 3:
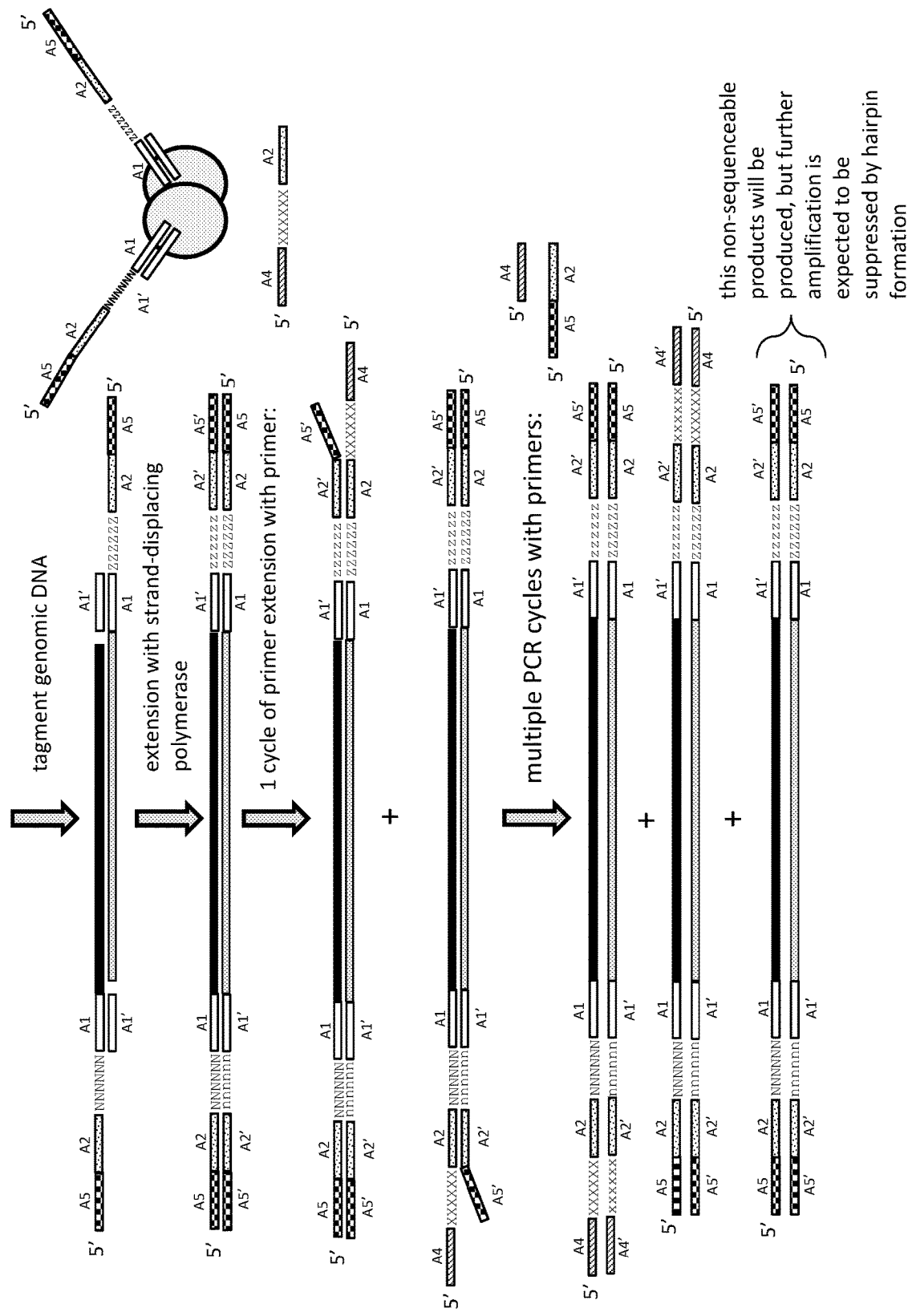
FIG. 3 schematically illustrates an exemplary transposase-based library preparation method that uses a molecular barcode.
Figure 4:
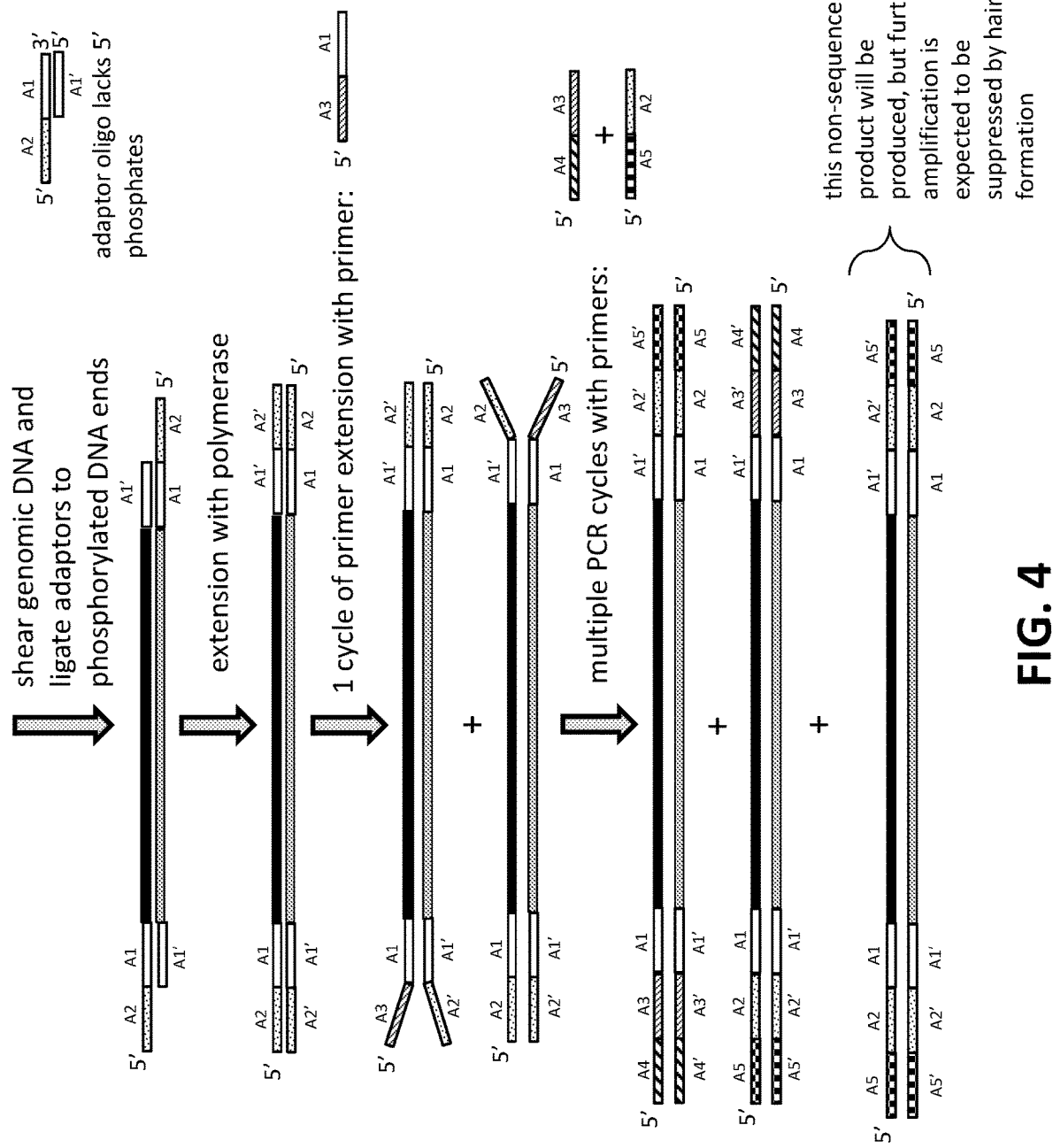
FIG. 4 schematically illustrates an exemplary ligation-based library preparation method.

The method may be implemented in a variety of different ways, examples of which are illustrated in FIGS. 2-9. For example, the library of step (a) may be made by tagmentation using a transposase (e.g. a Tn5 or Mu or Vibhar transposase) loaded with a single type of transposon end (which may or may not have a variable molecular barcode sequence therein), i.e., not a transposase loaded with multiple transposase ends. Alternatively, the library of (a) may made by ligating a single adaptor (which may or may not have a sample index sequence, or a variable molecular barcode sequence) to a population of cDNA or genomic fragments. Such cDNA or genomic fragments may be made by fragmenting an initial cDNA or genomic sample by physical, chemical or enzymatic means. Other samples (e.g., cfDNA) may be naturally fragmented. In these embodiments, the fragments may be end-repaired, blunted and A tailed prior to ligation to an adaptor that has a T overhang (see FIG. 6). In the case of transposition reaction, the A1 sequence directly appended to the target fragment may comprise the transposase recognition sequence, and may have a minimum required length. In ligation embodiments, the A1 sequence may be significantly shorter, and may comprise only a minimum sequence or length required to enable efficient ligation. In some embodiments, the target fragment is ligated to both the A1 and A1' strands. In some embodiments, the 5' ends of the adapter is not phosphorylated and cannot be ligated, suppressing adaptor-adaptor ligation. The method may be implemented using sequence tags that do not contain a molecular barcode (as illustrated in FIGS. 2 and 4). FIG. 2 illustrates an embodiment where the symmetrical library is made by tagmentation with a transposase containing a single type of oligo tag, where A1 (and its complement A1') comprises a transposase recognition sequence and A2 comprises a single stranded tail comprising a sequence identical to a primer A2. In some embodiments, the A1 sequence may comprise a sample index. In some embodiments, the A1' sequence may be modified at the 3' end (for example, with a 3' dideoxy nucleotide, or with a blocking chemical group on the 3' OH) to prevent extension by a polymerase. The complementary top and bottom strands of the target fragment or insert are shown in black and grey. After a single round of primer extension with a primer 5' A3-A1, a pair of duplex molecules is produced with one duplex end and one unpaired, Y-shaped end. Although these two duplex molecules are similar in structure, they differ in the orientation of the insert sequence, as A3-A1 is on the 5' end of the top strand (black) in one duplex molecule, and A3-A1 is on the 5' end of the bottom strand (grey) in the other molecule. In some embodiments, a limiting amount of the A3-A1 primer may be used, or the A3-A1 primer may be removed or destroyed before subsequent PCR steps. However, care must be taken to ensure that the A3-A1 primer is able to compete with intramolecular annealing of the A1 sequence with the A1' sequence (similar to the effect known as PCR suppression). Methods of modulating the effect of PCR suppression or enabling primer invasion into a hairpin portion of a duplex are known in the art, and include techniques such as adjusting primer concentration, adjusting primer sequence, using modified bases of nucleotides such as unstructured nucleic acids or Locked Nucleic acids, adjusting salt concentration, increasing template length, toehold primers as described in *J Am Chem Soc.* 2013 Apr. 17; 135(15):5612-9, and the like. Furthermore, in this invention, the primer extension reaction is only a single step (in contrast to PCR which typically has many cycles), and useful libraries will be produced even if this primer extension step is not 100% efficient.

After the primer extension step, the library may be amplified using a pair of primers comprising sequences A2 and A3. In some embodiments, the primers only contain the A2 and A3 sequences. In other embodiments (illustrated in FIG. 2), the A2 and A3 sequences may be joined to other primer or adapter sequences A4 and A5. In some embodiments, A4 and A5 may comprise sequences necessary for clonal amplification of the library, for example by bridge amplification, or in emulsion PCR. In some embodiments, the PCR primers may comprise sample index sequences corresponding to the sample of origin. The PCR primer A2 or A5-A2 will bind to templates containing the A2' sequence, and as can be seen in FIG. 2, some of these strands also contain the A2 sequence. Thus, some "hairpin" molecules may be formed in the PCR, which have A2 on one end and A2' on the other end. However, under standard PCR conditions, (for example, conditions described in the manuals for Herculase II of Pfu Ultra enzymes commercialized by Agilent Technologies) these molecules with self-annealing ends will be amplified less efficiently than the molecules with asymmetrical ends. In the exponential amplification conditions of a PCR reaction, the molecules with asymmetrical ends will easily outcompete the symmetrically tagged molecules. At the end of the PCR amplification in FIG. 2, two sequenceable molecules are formed: one with adapter A5 on the 5' end of the top strand (black), and adapter A4' on the 3' end of the top strand (black), and a second one with adapter A5 on the 5' end of the bottom strand (grey), and adapter A4' on the 3' end of the bottom strand (grey).

Figure 5:
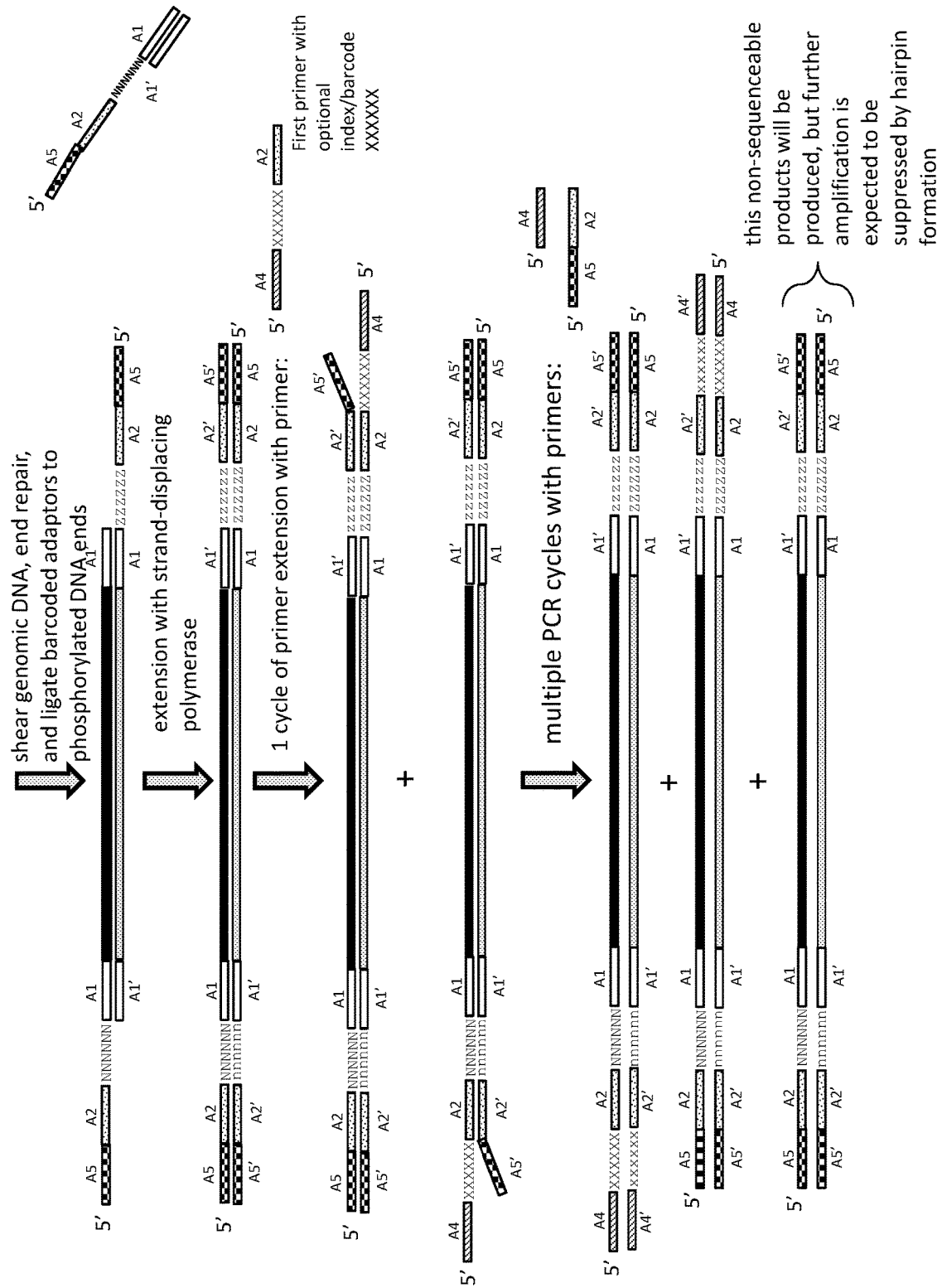
FIG. 5 schematically illustrates an exemplary ligation-based library preparation method that uses a molecular barcode.
Figure 6:
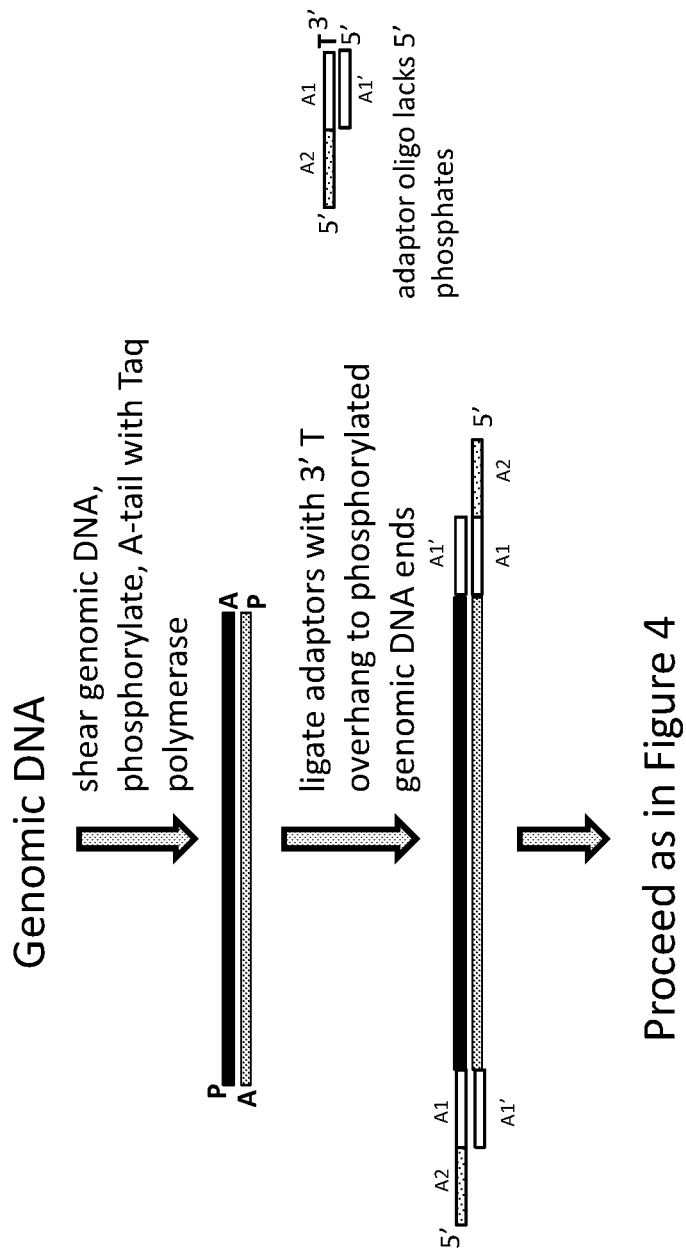
FIG. 6 schematically illustrates an exemplary ligation-based library preparation method that involves A-tailing. This protocol would also work with barcoded adapters (see FIG. 5).

In other embodiments, the method may be implemented using sequence tags that contain a molecular barcode (as illustrated by the "NNNNNN" and "ZZZZZZ" sequence in FIGS. 3 and 5). In these embodiments, the 5' and 3' sequence tags of (a) each comprise a molecular barcode that varies in sequence in the library. In most cases, the barcode added to each end of the molecule is different, that is, "NNNNNN" is complementary to "nnnnnn" which is different from "ZZZZZZ," which is complementary to "zzzzzz". One potential advantage of including the molecular barcode sequences is that because the NNN barcode sequence is not likely to be homologous to the zzz sequence on other end of the same strand, intramolecular hairpin formation may be less favorable, or the hairpin may be easier to invade with a primer. In some embodiments, the molecular barcodes may each have a random sequence, e.g., of 4 to 12 nucleotides in length, however a lower or higher complexity barcode may be used in many cases. In some embodiments, the sample index, molecular barcodes, and target sequence or insert may be sequenced by using different sequencing primers which anneal to the adjacent sequences. In other embodiments, one or more of these features may be sequenced by a long sequencing read primed from a single location.

In some embodiments, the 5' tail of the first primer of (b) may also comprise a molecular barcode or a sample index that varies in sequence (as illustrated by the "XXXXXX" sequence in FIGS. 3 and 5). Again, this molecular barcode may have a random sequence, e.g., of 4 to 12 nucleotides in length, or it may comprise a set of known sequences used to distinguish different samples of origin, or a combination of these types of barcode; a lower or higher complexity barcode can be used in many cases. Alternatively, a single primer sequence which does not contain a molecular or sample barcode may be used. In these embodiments, some of the products of the amplification step (d) may have a top strand that contains, from 5' to 3', the molecular barcode/sample index in the 5' tail of the first primer of (b) (i.e., the "XXXXXX" sequence), the barcode sequence "NNNNNN", the sequence of a fragment, and the complement of the barcode in the 5' sequence tag (the "zzzzzz" sequence). Also, some of the products of the amplification step may have a bottom strand that contains from 5' to 3', the molecular barcode/sample index in the 5' tail of the first primer of (b) (i.e., the "XXXXXX" sequence), the barcode sequence "ZZZZZZ", the sequence of a fragment complementary to the top strand, and the complement of the barcode in the 5' sequence tag (the "nnnnnn" sequence). Notably, these two types of fragments may both be amplified or copied in a clonal amplification (such as bridge PCR, Wildfire amplification, emulsion PCR, or the like) and separately sequenced. However, after sequencing, the dual molecular barcodes NNNNNN and ZZZZZZ and their complements nnnnnn and zzzzzz may be used to determine the sequence of the original Watson and crick strands of the template. Related methods and the avantages are described as Duplex sequencing by SR Kennedy et al. *Nat Protoc* 2014 Oct. 9; 9(11):2586-606.

The complexity of any molecular barcode may be at least 4, at least 5, at least 6, at least 8, at least 10, at least 12, at least 24, at least 96, at least 384, at least $10^3$, at least $10^4$ or at least $10^5$. In embodiments where more than one molecular barcode is used on one template molecule (e.g., the ZZZ and NNN sequences in FIG. 3), the complexity of one or both individual barcodes may be chosen to be lower, while preserving complexity by the combination of multiple barcodes.

The primer extension step (c) may be done once or, in some embodiments, twice (e.g., using a thermostable polymerase and thermocycling the reaction) and in some embodiments, the method may comprise removing, inactivating, or destroying any unextended first primer between steps (c) and (d). For example, this can be conveniently done by passing the reaction through a size exclusion column, blocking the 3' ends of the primers and fragments to prevent further extension, or digestion with a nuclease specific for single stranded DNA, although a myriad of alternative methods are available. In other embodiments, a limiting amount of the first primer can be used and, as such, the method can be performed without removing, inactivating, or destroying any unextended first primer between steps (c) and (d).

In some embodiments, the library of step (a) may be made by (i) making an initially tagged library comprising fragments of cDNA or genomic DNA that comprise sequence tags on both ends, wherein the sequence tags comprise a single-stranded region (e.g., by tagging the fragments with a partially single-stranded adaptor sequence). See, e.g., FIG. 6. In these embodiments, as shown, the 3' ends can be extended by a polymerase, thereby making the single-strand region double-stranded. Depending on how the method is implemented, the 3' ends may be extended using a strand-displacing polymerase or a non-strand-displacing polymerase. In some embodiments, the single strand region that is made double stranded by the polymerase may contain a single-stranded molecular barcode. In these embodiments, the extending may convert the single-stranded molecular barcode into a double-stranded molecular barcode. Double stranded barcodes made in these ways allow the bottom strands of the fragments to be tagged with the complement of the barcode of the top strands of the same fragment, which can be useful for identifying sequence reads that are from the top and bottom strands of the same double-stranded fragment. Complex or random barcodes that are double stranded, which are often used in library construction, can be challenging to make by other methods (e.g., by annealing oligonucleotides together).

Figure 7:
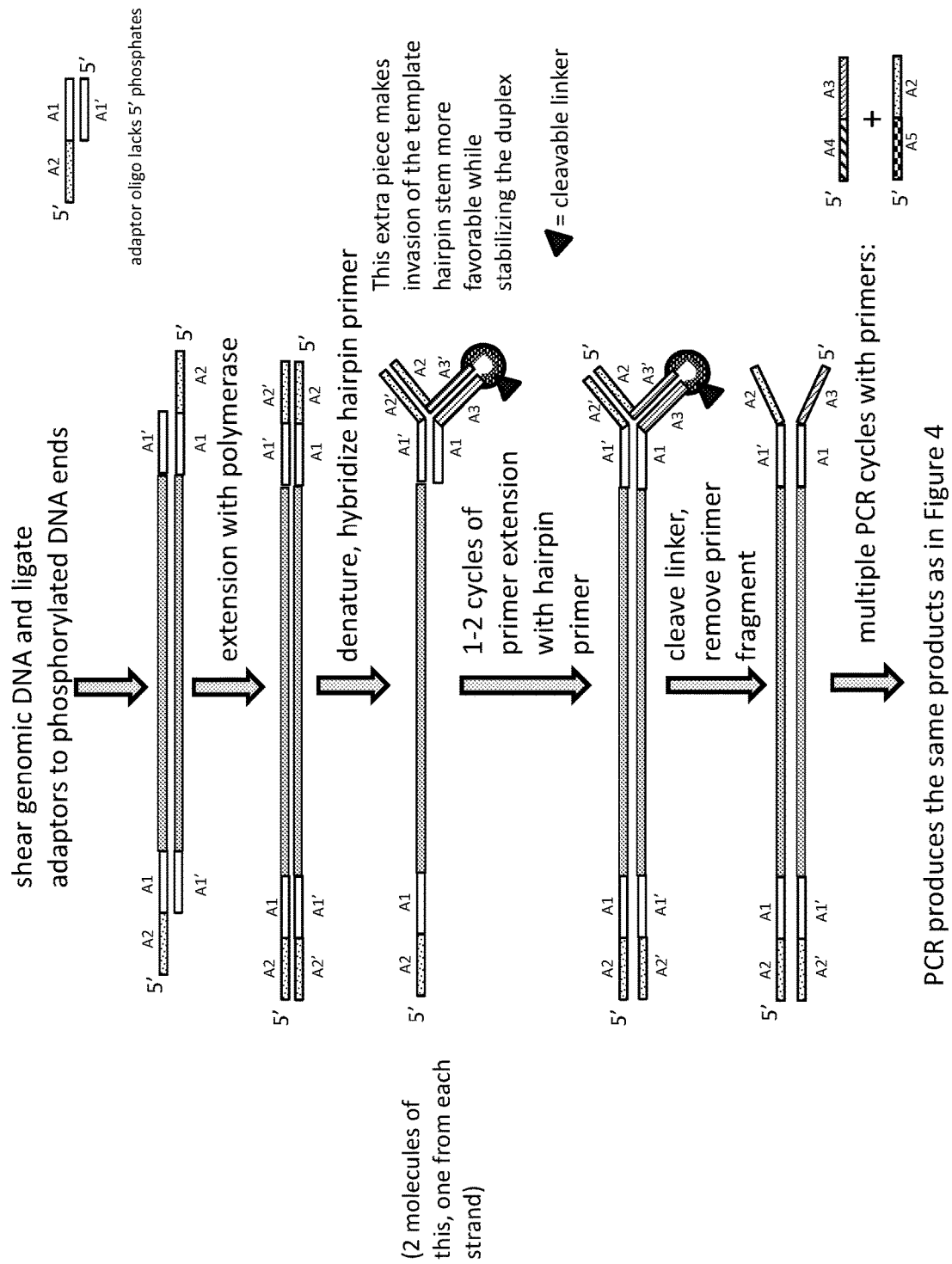
FIG. 7 schematically illustrates an exemplary ligation-based library preparation method that uses a hairpin oligonucleotide.
Figure 8:
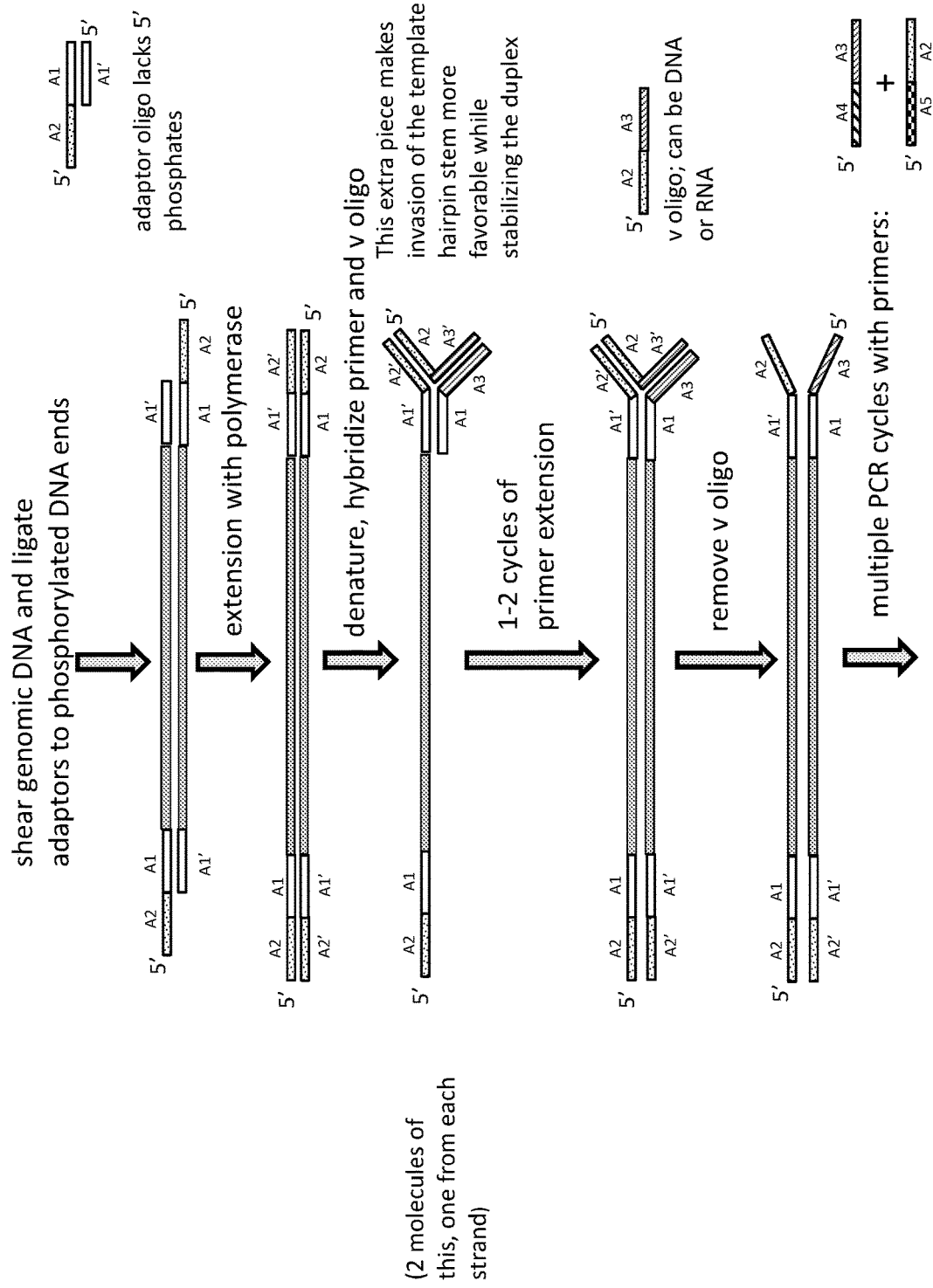
FIG. 8 schematically illustrates an exemplary ligation-based library preparation method that employs a "V" oligonucleotide.
Figure 9:
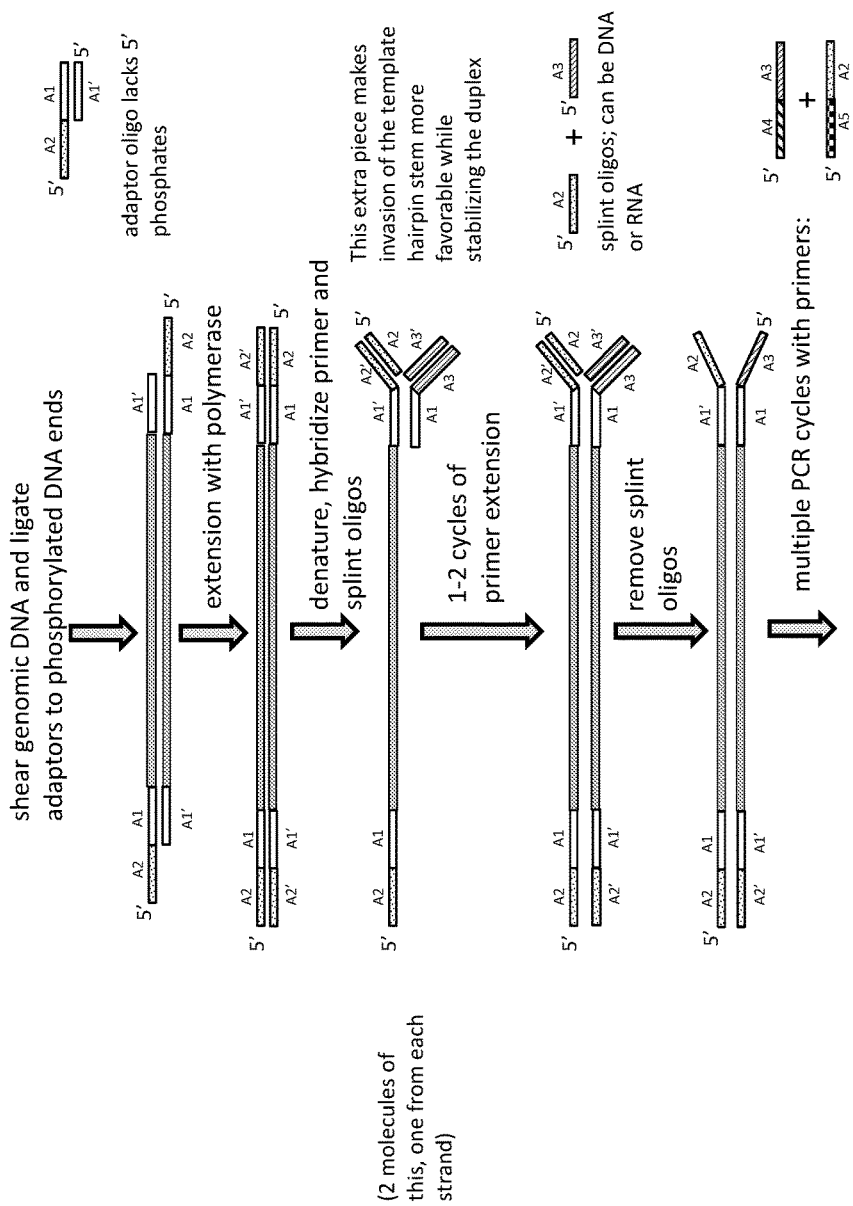
FIG. 9 schematically illustrates an exemplary ligation-based library preparation method that uses a splint oligonucleotide.

FIGS. 7 to 9 show alternative implementations of the method that employ a hairpin oligonucleotide. FIG. 7 shows an embodiment in which the first primer has two regions that hybridizes to the 3' sequence tag, separated by a hairpin, e.g., of sequence A3. FIG. 8 shows an embodiment in which a "V" oligonucleotide that hybridizes to the 3' sequence tag and the first primer is used. FIG. 9 shows an embodiment that employs splint oligonucleotides. In some of these embodiments, additional sequences A2 and sequences complementary to A3 are added during hybridization step (b). In some embodiments, the additional sequences are part of the same oligonucleotide. In these embodiments, one or more of the 3' end of the additional sequences cannot be extended by a polymerase.

As would be apparent, after the asymmetric library is made, the library may be analyzed, e.g., sequenced. In some embodiments, this may comprise hybridizing the library with a substrate that contains primers that hybridize to the A4 and A5 sequences or a complement thereof, amplifying at least some of the hybridized sequences on the substrate by bridge PCR, then sequencing the bridge PCR products. In these embodiments, the A4 and A5 sequences could be the P5 and P7 sequences used in the Illumina sequence platform, or a complement thereof. In some embodiments, the library may be amplified with another pair of tailed primers, hybridized to a substrate that contains primers that hybridize to or has a sequence in the tails of those primers, amplifying the hybridized sequences by bridge PCR and then sequencing the bridge PCR products. In some embodiments, the A4 and A5 sequences sequences may enable amplification by emulsion PCR. In some embodiments, the A4 and A5 sequences may be compatible with the next generation sequencing platform being used to sequence the library. Alternatively, the library may be amplified using primers that have tail sequences that are compatible with the next generation sequencing platform being used to sequence the library. The products may be sequenced using any suitable method including, but not limited to Illumina's reversible terminator method.

In certain embodiments, the initial DNA being analyzed may be derived from a single source (e.g., a single cell, organism, virus, tissue, cell, subject, etc.), whereas in other embodiments, the nucleic acid sample may be a pool of nucleic acids extracted from a plurality of sources (e.g., a pool of nucleic acids from a plurality of single cells, organisms, tissues, cells, subjects, etc.), where by "plurality" is meant two or more. As such, in certain embodiments, a tagged sample may be combined with tagged samples from other sources, e.g., 2 or more sources, 3 or more sources, 5 or more sources, 10 or more sources, 50 or more sources, 100 or more sources, 500 or more sources, 1000 or more sources, 5000 or more sources, up to and including about 10,000 or more sources, where the molecular barcode of the tags allows the sequences from different sources to be distinguished after they are analyzed.

EXAMPLE

A variation of the experiment outlined in FIG. 1 was performed. In this version, a multiplex PCR strategy was used, and a set of multiple PCR primers was used for amplification. However, the main feature of the invention, creating an asymmetrical sequencing library from a symmetrically-tagged library, is not dependent on the use of this multiplex PCR strategy. 50 ng of human genomic DNA was incubated with 100 ng of purified, duplex DNA-loaded *Vibrio harveyi* transposase in fragmentation buffer from Agilent's SureSelectQXT library prep kit (catalog # G9682A). We used six different transposase duplexes mixed in equal amounts. The duplex sequences were composed of one short 19mer strand (CTGTCTCTTGATCACAAGT; SEQ ID NO: 20) hybridized to each of six different long strands of 47 or 48 bases in length. The sequences of the long strands were:

SEQ ID NO. 1:
5' TAGCTTGGCTATCGACACCATAAGGCGAACTTGTGATCAAGAGACAG

SEQ ID NO. 2:
5' CTAATCTGATGGACGGACACACGTACTAGACTTGTGATCAAGAGACAG

SEQ ID NO. 3:
5' CGATAGTTATGCGAGCACCACTAGGCATGACTTGTGATCAAGAGACAG

SEQ ID NO. 4:
5' GATGTGATCGTACCGACACAGGACTCCTACTTGTGATCAAGAGACAG

SEQ ID NO. 5:
5' AGTTCATGACGTGTGACCACCTCTCTATACTTGTGATCAAGAGACAG

SEQ ID NO. 6:
5' CAGGAGTCCGTTATCACACATATCCTCTACTTGTGATCAAGAGACAG

The tagmentation reaction of the genomic DNA with the six different loaded transposases was incubated at 45 C for 10 minutes, followed by 4 C for 2 minutes. The reaction was stopped by adding 1.6 volumes of Stop Buffer (Agilent SureSelectQXT library kit, # G9682A). The tagmented genomic DNA was purified using AMPure beads (Beckman Coulter) according to the manufacturer's protocol, and eluted in 11 μl water. The first adapter (Adapter A) was then added to one end of the genomic fragments using two cycles of primer extension. 10 μl of the above tagmentation product was mixed with 0.5 μl Herculase II Fusion enzyme (Agilent Technologies), 5 μl 5× Herculase II Reaction Buffer, 0.25 μl dNTPs (25 mM each), 1.25 μl DMSO, 6 μl of Adapter A primer cocktail, and 2 μl water. Adapter A primer cocktail was composed of six primer sequences (15 μM combined):

SEQ ID NO. 7:
5' ATTCAGTGAGATGCACCACACAGAGTAAGGCGAACTTGTGATCAAGA GACAG

SEQ ID NO. 8:
5' ATTCAGTGAGATGCACCACACAGAGCGTACTAGACTTGTGATCAAGA GACAG

SEQ ID NO. 9:
5' ATTCAGTGAGATGCACCACACAGAGTAGGCATGACTTGTGATCAAGA GACAG

SEQ ID NO. 10:
5' ATTCAGTGAGATGCACCACACAGAGGGACTCCTACTTGTGATCAAGA GACAG

SEQ ID NO. 11:
5' ATTCAGTGAGATGCACCACACAGAGCTCTCTATACTTGTGATCAAGA GACAG

SEQ ID NO. 12:
5' ATTCAGTGAGATGCACCACACAGAGTATCCTCTACTTGTGATCAAGA GACAG

The reaction went for 2 minutes at 68° C., then 30 seconds at 98° C., then for two cycles of (98° C. for 30 seconds; 56° C. for 30 seconds; 72° C. for 1 minute), followed by an incubation at 72° C. for 3 minutes, before cooling to 4° C. The resulting products were purified on AMPure beads (Beckman Coulter) according to the manufacturer's protocol, and eluted in 11 μl water.

10 μl of the primer extension reaction was then used in a PCR reaction to add the P5 and P7 primer sequences. To the 10 μl reaction products were added 1 μl Herculase II Fusion Enzyme (Agilent Technologies), 10 μl 5× Herculase II reaction buffer, 0.5 μl dNTPs (25 mM each), 2.5 μl DMSO, 3 μl primer cocktail B (6 primers at a total concentration of 15 μM combined), 3 μl (15 μM) Primer C (SEQ ID NO. 13: 5'CAAGCAGAAGACGGCATACGAGATAGTCCGAC-GATCATTCAGTGAGATGCACC ACACAGAG), and 20 μl water. Primer cocktail B contained the following sequences:

SEQ ID NO. 14:
5'AATGATACGGCGACCACCGAGATCTACACCGACAGGTTCAGTAGCTTGG CTATCGACACCATAAG

SEQ ID NO. 15:
5'AATGATACGGCGACCACCGAGATCTACACCGACAGGTTCAGCTAATCTG ATGGACGGACACACGTA

SEQ ID NO. 16:
5'AATGATACGGCGACCACCGAGATCTACACCGACAGGTTCAGCGATAGTT ATGCGAGCACCACTAGG

SEQ ID NO. 17:
5'AATGATACGGCGACCACCGAGATCTACACCGACAGGTTCAGGATGTGAT CGTACCGACACAGGAC

SEQ ID NO. 18:
5'AATGATACGGCGACCACCGAGATCTACACCGACAGGTTCAGAGTTCATG ACGTGTGACCACCTCT

-continued

SEQ ID NO. 19:
5'AATGATACGGCGACCACCGAGATCTACACCGACAGGTTCAGCAGGAGTC

CGTTATCACACATATC

PCR was then carried out by heating the reaction at 98° C. for 30 seconds, then proceeding with four cycles of (98° C. for 30 seconds, 56° C. for 30 seconds, and 72° C. for 1 minute), followed by 3 minutes at 72° C., then holding at 4° C.

Following PCR, and aliquot of the reaction was analyzed on a High-Sensitivity Bioanalyzer chip (Agilent Technologies). Bioanalyzer analysis showed that a library of fragments averaging 600 bases in length was produced. 11.5 femtomoles of the reactions were then sequenced using a 150v3 Illumina MiSeq kit (2×75 cycles) according to the manufacturer's specifications. Sequencing results found that 98.8% of the human genomic DNA reads were unique, which is similar to the 98.5% unique reads achieved using the Agilent SureSelectQXT library kit. We achieved 56.5% coverage of the human genome per 10 million reads, which is slightly better than the 53.4% coverage achieved using the Agilent SureSelectQXT library kit.

EMBODIMENTS

Embodiment 1

A method for making an asymmetrically-tagged sequencing library, comprising:

(a) obtaining a symmetrically-tagged library of cDNA or genomic DNA fragments, wherein at least some of the members of the library comprise a top strand comprising a 5' sequence tag and a 3' sequence tag, wherein the 5' and 3' sequence tags complementary sequences;

(b) hybridizing a first primer to a region of the 3' sequence tag of the library, wherein the first primer comprises a 3' region which is complementary to said region of the 3' sequence tag of the library, and a 5' non-complementary tail;

(c) extending the first primer to produce primer extension products that comprises, from 5' to 3', the sequence of the first primer, a sequence of a fragment, and the complement of a 5' sequence tag of (a); and (d) amplifying the primer extension products of (c) using:
  i. a forward primer comprising sequence A4, e.g., a forward primer of formula A4-A3, wherein sequence A4 is a 5' tail and sequence A3 is contained in the sequence of the first primer; and
  ii. a reverse primer of formula A5-A2, wherein sequence A5 is a 5' tail and sequence A2 is contained in the 5' sequence tag of (a);

to produce an asymmetrically-tagged library in which at least some of the members comprise a top strand comprising i. a first end comprising sequence A5, ii. the sequence of a fragment, and ii. a second end comprising the complement of sequence A4.

Embodiment 2

The method of embodiment 1, wherein the 5' and 3' sequence tags of (a) each comprise a double-stranded molecular barcode that varies in sequence in the library.

Embodiment 3

The method of any prior embodiment, wherein the molecular barcodes are random sequences.

Embodiment 4

The method of any prior embodiment, wherein the 5' tail of the first primer of (b) comprises a sample index that varies in sequence.

Embodiment 4A

The method of any prior embodiment, further comprising analyzing the products of step (d).

Embodiment 4B

The method of embodiment 4A, wherein the analyzing comprises sequencing the products of step (d).

Embodiment 5

The method of embodiment 4, wherein the molecular barcode is a random sequence.

Embodiment 6

The method of embodiment 4, wherein the molecular barcode of the 5' sequence tag, but not the barcode of the 3' sequence tag, is copied in the primer extension step (c), and wherein the products of amplification step (d) contain the molecular barcode in the 5' tail of the first primer of (b), the sequence of a fragment, and the complement of the barcode in the 5' sequence tag.

Embodiment 7

The method of any prior embodiment, wherein the method comprises removing, inactivating, or destroying any unextended first primer between steps (c) and (d).

Embodiment 8

The method of any prior embodiment, wherein the library of (a) is made by tagmentation.

Embodiment 9

The method of any prior embodiment, wherein the tagmentation is done using a Tn5, Mu, or Vibhar transposase.

Embodiment 10

The method of any prior embodiment, wherein the library of (a) is made by ligating adaptors to a population of cDNA or genomic fragments.

Embodiment 11

The method of embodiment 10, wherein the cDNA or genomic fragments are made by fragmenting an initial cDNA or genomic sample by physical, chemical or enzymatic means.

Embodiment 12

The method of any prior embodiment, wherein the library of step (a) is made by (i) making an initially tagged library comprising fragments of cDNA or genomic DNA that comprise sequence tags on both ends, wherein the sequence tags comprise a single-stranded region, and (ii) extending at least some of the 3' ends of the initially tagged library to make the single-stranded region double-stranded.

Embodiment 13

The method of embodiment 12, wherein the single strand region contains a single stranded molecular barcode, and wherein the extending converts the single stranded molecular barcode into a double stranded molecular barcode.

Embodiment 14

The method of embodiment 13, wherein the extending is done using a strand-displacing polymerase.

Embodiment 15

The method of embodiment 13, wherein the extending is done using a non-strand-displacing polymerase.

Embodiment 16

The method any prior embodiment, further determining the sequence of two or more molecular barcodes on the same molecule.

Embodiment 17

The method of embodiment 16, wherein the analyzing comprises sequencing the products of step (d).

Embodiment 17A

The method of any prior embodiment, further comprising using said molecular barcode sequences to associate sequencing reads from the top strand of a duplex with sequencing reads from the complementary strand.

Embodiment 17B

The method of any prior embodiment, wherein sequence information is obtained from both the top strand and from the bottom strand of a duplex Embodiment 18. The method of any prior embodiment, wherein additional sequences A2 and sequences complementary to A3 are added during hybridization step (b).

Embodiment 19

The method of embodiment 18, wherein the additional sequences are part of the same oligonucleotide.

Embodiment 20

The method of embodiment 18, wherein one or more of the 3' end of said additional sequences cannot be extended by a polymerase.

Embodiment 21

The method of any prior embodiment, wherein the tags are in the range of 4 to 12 nucleotides in length.

Embodiment 22

The method of any prior embodiment, wherein the method comprises repeating steps (b) and (c) before step (d).

Embodiment 23

The method of any prior embodiment, wherein the method comprises using two or more molecular barcodes.

Embodiment 24

The method of any prior embodiment, wherein the method comprises using one or more molecular barcodes in combination with one or more sample index sequences.

Embodiment 25

The method of any prior embodiment, wherein the method comprises using the sequence of one or more molecular barcodes and their complementary sequences to correct sequencing errors and/or determine the sequence of the original duplex template.

Embodiment 26

The method of any prior embodiment, wherein the method comprises identifying one or more sequence reads as corresponding to the top strand of a target fragment, and identifying one or more sequence reads as corresponding to the bottom strand of a target fragment.

Embodiment 27

The method of any prior embodiment, wherein the method comprises associating the sequencing information from the top strand and the sequencing information from the bottom strand to provide sequence information corresponding to both ends of the target fragment.

Embodiment 28

The method of any prior embodiment, wherein the method comprises using sequence information from both the top and bottom strands to correct polymerase errors, detect rare mutations, or to detect insertions, deletions, inversions, or translocations.

The invention claimed is:

1. A method for making an asymmetrically-tagged sequencing library, comprising:
   (a) obtaining a symmetrically-tagged library of cDNA or genomic DNA fragments, wherein at least some of the members of the library comprise a top strand comprising a 5' sequence tag and a 3' sequence tag, wherein the 5' and 3' sequence tags comprise complementary sequences;
   (b) hybridizing a first primer to a region of the 3' sequence tag of the library, wherein the first primer comprises a 3' region which is complementary to said region of the 3' sequence tag of the library, and a 5' non-complementary tail;
   (c) extending the first primer to produce primer extension products that comprise, from 5' to 3', the sequence of the first primer, a sequence of a fragment, and the complement of a 5' sequence tag of (a); and
   (d) amplifying the primer extension products of (c) using:
      i. a forward primer comprising sequence A4; and
      ii. a reverse primer of formula A5-A2, wherein sequence A5 is a 5' tail and sequence A2 is contained in the 5' sequence tag of (a);
   to produce an asymmetrically-tagged library in which at least some of the members comprise a top strand comprising i. a first end comprising sequence A5, ii. the sequence of a fragment, and iii. a second end comprising the complement of sequence A4.

2. The method of claim 1, wherein the 5' and 3' sequence tags of (a) each comprise a double-stranded molecular barcode that varies in sequence in the library.

3. The method of claim 2, wherein the molecular barcodes are random sequences.

4. The method of claim 1, wherein the 5' tail of the first primer of (b) comprises a sample index that varies in sequence.

5. The method of claim 1, further comprising analyzing the products of step (d).

6. The method of claim 5, wherein the analyzing comprises sequencing the products of step (d).

7. The method of claim 6, further determining the sequence of two or more molecular barcodes on the same molecule.

8. The method of claim 7, further comprising using said molecular barcode sequences to associate sequencing reads from the top strand of a duplex with sequencing reads from the complementary strand.

9. The method of claim 6, wherein sequence information is obtained from both the top strand and the bottom strand of a duplex.

10. The method of claim 1, wherein the method comprises removing, inactivating, or destroying any unextended first primer between steps (c) and (d).

11. The method of claim 1, wherein the library of (a) is made by tagmentation.

12. The method of claim 11, wherein the tagmentation is done using a Tn5 or Vibhar transposase.

13. The method of claim 1, wherein the library of (a) is made by ligating adaptors to a population of cDNA or genomic fragments.

14. The method of claim 13, wherein the cDNA or genomic fragments are made by fragmenting an initial cDNA or genomic sample by physical, chemical or enzymatic means.

15. The method of claim 1, wherein the library of step (a) is made by (i) making an initially tagged library comprising fragments of cDNA or genomic DNA that comprise sequence tags on both ends, wherein the sequence tags comprise a single-stranded region, and (ii) extending at least some of the 3' ends of the initially tagged library to make the single-stranded region double-stranded.

16. The method of claim 15, wherein the single strand region contains a single stranded molecular barcode, and wherein the extending converts the single stranded molecular barcode into a double stranded molecular barcode.

17. The method of claim 16, wherein the extending is done using a strand-displacing polymerase.

18. The method of claim 16, wherein the extending is done using a non-strand-displacing polymerase.

19. The method of claim 1, wherein additional sequences A2 and sequences complementary to A3 are added during hybridization step (b).

20. The method of claim 19, wherein one or more of the 3' ends of said additional sequences cannot be extended by a polymerase.

* * * * *